Figure 1:
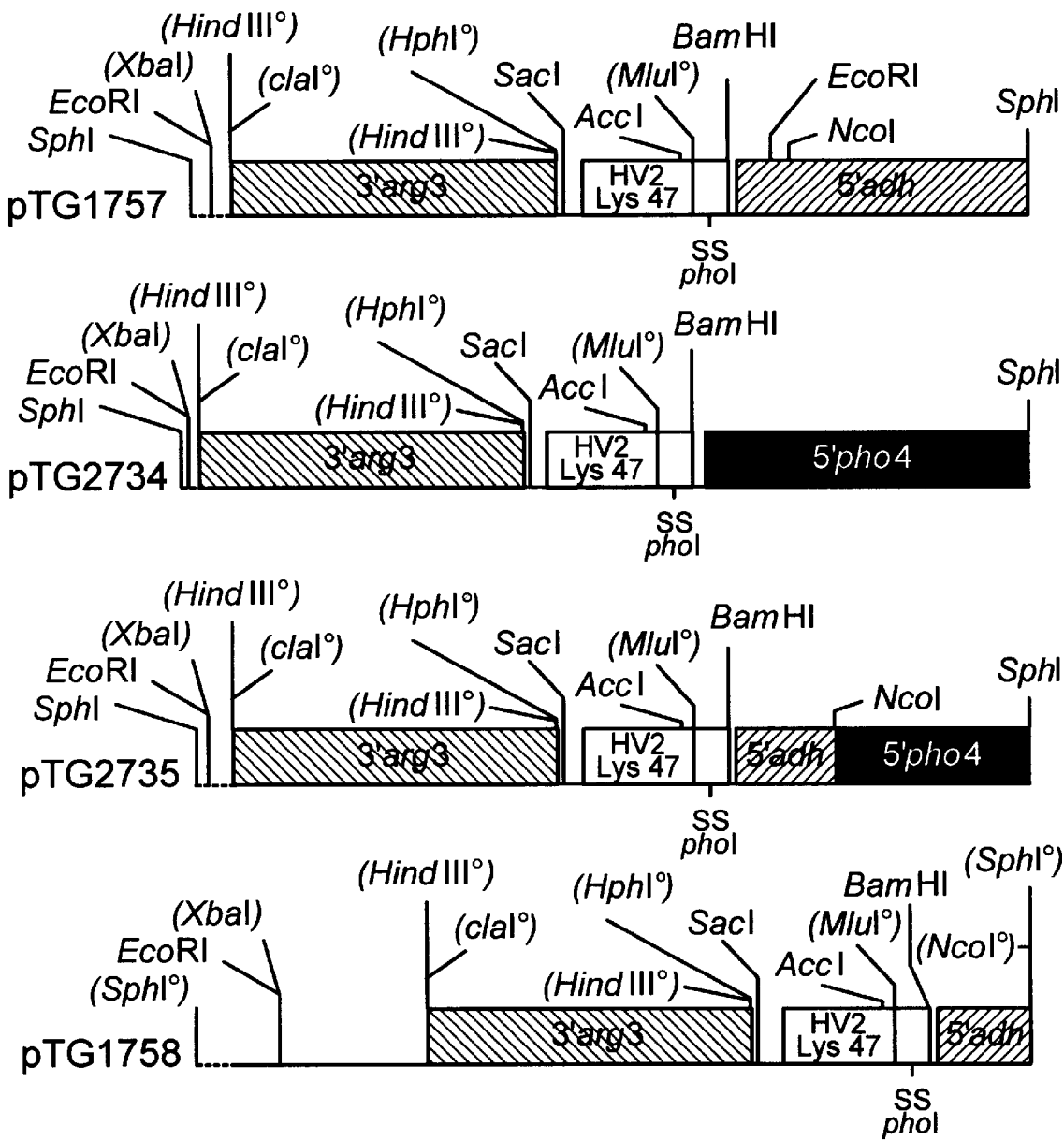

United States Patent [19]

Jacobs et al.

[11] Patent Number: 5,834,237
[45] Date of Patent: Nov. 10, 1998

[54] COMBINED USE OF TWO EXPRESSION CASSETTES FOR THE PRODUCTION OF A PROTEIN OF INTEREST

[75] Inventors: Eric Jacobs, Dorlisheim; Nathalie Silvestre, Strasbourg, both of France; Ernst Schweinbryber, Bern, Switzerland

[73] Assignee: Transgene S.A., Strasbourg, France

[21] Appl. No.: 714,070

[22] PCT Filed: Mar. 9, 1995

[86] PCT No.: PCT/FR95/00269

§ 371 Date: Oct. 7, 1996

§ 102(e) Date: Oct. 7, 1996

[87] PCT Pub. No.: WO95/24491

PCT Pub. Date: Sep. 14, 1995

[30] Foreign Application Priority Data

Mar. 10, 1994 [FR] France ................................. 94 02767

[51] Int. Cl.⁶ ....................................................... C12P 21/06
[52] U.S. Cl. ................ 435/69.1; 435/172.3; 435/254.11; 435/254.21; 536/23.1; 536/24.1
[58] Field of Search ................. 536/23.1, 24.1; 435/320.1, 254.21, 69.1

[56] References Cited

PUBLICATIONS

DATABASE EMBL, X77512, 7 Feb. 1994, H. Frankhauser et al, Thiamine repressible genes regulatory protein THI1 (Transcription factor NTF1), & Journal of Biological Chemistry, vol. 269, 1994 MD US, pp. 11921–11926.

J. BIOL. CHEM. (1994), 269(16), 11921–6, CODEN; JBCHA3;ISSN: 0021–9258, Apr. 1994, Tang, Carol S.L. et al, "ntfl+ encodes a 6–cysteine zinc finger–containing transcription factor that regulates the nmtl promoter in fission yeast".

DATABASE WPI, Section CH, Week 9340, Derwent Publications Ltd., London, GB; Class B04, AN 93–314182 & IT–B–1 236 844, 22 Apr. 1993.

FEBS Lett. (1992), 305(3), 244–8 CODEN: FEBLAL;ISSN: 0014–5793, K. Nosaka et al, "Upstream activation element of ther PH03 gene encoding thiamin — repressible acid phosphatase in Saccaromyces cerevisiae".

GENETICS (1992), 130(3), 445–9 CODEN: GENTAE;ISSN: 0016–6731, Anne Marie Scheingruber et al, "Isolation and characterization of regulatory mutants from Schizosaccharomyces pombe involved in thiamine–regulated gene expression".

GENE (1993), 123(1), 127–30 CODEN: GENED6;ISSN: 0378–1119. Kinsey Maundrell, "Thiamin–repressible expression vectors pREP and pRIP for fission yeast".

FEBS Letters, vol. 297, No. 1,2, Feb. 1992 AMSTERDAM NL, pp. 155–158, Hiroshi Nishimura et al, "Cloning and characteristics of a positive regulatory gene, THI2(PH06), of thiamin biosynthesis in Saccaromyces cerevisiae".

J. BACTERIOL. (1994), 176(21), 6631–5 CODEN: JOBAAY;ISSN: 0021–9193, Andreas Zurlinden et al, "Cloning, nucleotide sequence, and regulation of Schizosaccharomyces pombe thi4, a thiamine biosynthetic gene".

GENE (1994), 147(1), 141–4 CODEN: GENED6;ISSN: 0378–1119, Hans Fankhauser et al, "Thiamine –repressible genes in Schizosaccharomyces pombe are regulated by a Cys6 zinc–finger motif–containing protein".

Basi, G., et al., 1993, Gene, vol. 123, pp. 131–136, 1993.

Giniger, E., et al., 1985, Cell, vol. 40, pp. 767–774, 1985.

Yang, J., et al., 1990, Current Genetics, vol. 18, pp. 269–272, 1990.

Primary Examiner—Nancy Degen
Assistant Examiner—Irem Yucel
Attorney, Agent, or Firm—Burns, Doane, Swecker & Mathis, L.L.P.

[57] ABSTRACT

The present invention relates to a system for producing a protein of interest in a host cell comprising the combined use of two expression cassettes, one of which is for expressing a useful DNA fragment controlled by a thiamine-regulable promoter region, while the other is for expression an activator gene. The present invention also concerns expression cassettes comprising a useful DNA fragment controlled by a promoter region derived from the *Schizosaccharomyces pombe* pho-4 gene, as well as the vectors and cells comprising such an expression cassette. A novel method for the production of a useful protein is also provided.

34 Claims, 3 Drawing Sheets

COMBINED USE OF TWO EXPRESSION CASSETTES FOR THE PRODUCTION OF A PROTEIN OF INTEREST

The present invention relates to the biotechnology field, in particular to an improvement made to the production of a heterologous protein of commercial or therapeutic importance in a eukaryotic cell, and especially a yeast of the genus Schizosaccharomyces. It relates in the first place to the use of a gene coding for a product capable of activating a thiamine-regulable promoter region, thiamine governing the expression of the protein of interest, and in the second place to an expression cassette in which the DNA fragment coding for the protein of interest is placed under the control of a promoter region isolated or derived from the *Schizosaccharomyces pombe* pho4 gene.

For some years now, numerous expression cassettes for the production of proteins of interest in eukaryotic cells have been described in the literature. These cassettes comprise, in particular, a promoter region which is functional in the cell in question. Generally speaking, a promoter region is located in the 5' flanking region of the genes, and comprises the set of elements permitting the transcription of a DNA fragment placed under their control. A promoter region may also consist of the assembly of elements of various origins which are functional in the host cell, such as, in particular:

- a minimal promoter region comprising the TATA box and the transcription startsite. While it appears to be necessary for a correct initiation of transcription, it cannot on its own provide for an effective transcription; and
- regions located upstream of the TATA box which make it possible to provide for an effective level of transcription, either constitutively (transcription level constant throughout the cell cycle, irrespective of the culture conditions), or regulably (so-called regulatory regions permitting an activation of transcription in the presence of an activator and/or repression of transcription in the presence of a repressor), according to the gene from which they originate.

When it is desired to obtain a large amount of a protein of interest, a strong and constitutive promoter region is generally used to control the expression of the DNA fragment coding for the protein of interest, for example the 5' flanking regions of the Saccharomyces cerevisiae PGK (3-phosphoglycerate kinase) gene (Hitzeman et al., 1983, Science, 219, 620–625) and the *Schizosaccharomyces pombe* and (alcohol dehydrogenase) gene (Russel and Hall, 1983, J. Biol. Chem., 258, 143–149).

However, the use of a strong and constitutive promoter region is not suited to the production of proteins of interest displaying some degree of toxicity with respect to the host cell. In effect, the production of toxic proteins affects cell growth and risks bringing about the selection of spontaneous mutations leading to a loss or a significant reduction in the level of production. In extreme cases, cell viability may be affected.

For these reasons, it can be advantageous to have at one's disposal regulable promoter regions enabling the production of the protein of interest to be varied in accordance with the culture conditions or the cellular growth phase. Generally speaking, such promoter regions are isolated or are derived from regulable genes.

Over the last few years, a number of regulable genes have been demonstrated in numerous eukaryotes, and in particular in *Schizosaccharomyces pombe*. A wide variety of mechanisms govern the regulation of these genes. As examples of regulable *Schizosaccharomyces pombe* genes, there may be mentioned the heat shock genes whose expression increases with temperature (Gallo et al., 1991, Mol. Cell. Biol., 11, 281–288), and the gene coding for the enzyme fructosebiphosphatase [sic] (fbp) for which transcription is repressed in the presence of glucose and induced under conditions of glucose deficiency (Hoffman and Winston, 1989, Gene, 84, 473–479). Other members of this category include the thiamine-regulable genes, namely the pho4 (Yang and Schweingruber, 1990, Curr. Genet., 18, 269–272), nmt1 (Maundrell, 1990, J. Biol. Chem., 265, 10857–10864) and thi2 (Zurlinden and Schweingruber, 1992, Gene, 117, 141–143) genes whose expression is regulated at transcriptional level by thiamine, more precisely repressed in the presence of thiamine and induced or derepressed in its absence.

The regulatory regions of the promoter region of the pho4 gene which are involved in the response to thiamine have now been characterized, and regulable expression cassettes for the production of proteins of interest in Schizosaccharomyces have been generated. Yeasts harboring such an expression cassette are cultured in a medium supplemented with thiamine when culturing is directed only towards their propagation. As soon as culturing is undertaken for the purpose of producing a protein of interest, the yeasts are transferred to a medium lacking thiamine. Thus, when these regions are placed upstream of a DNA fragment coding for the Lys 47 variant of hirudin, an effective expression is obtained in the absence of thiamine, at least equivalent to the expression detected with the strong promoter region of the adh gene. Furthermore, their use in a cassette for the expression of the CFTR (cystic fibrosis transmembrane regulator) protein has enabled the latter to be produced by recombinant techniques despite being toxic in *Schizosaccharomyces pombe*.

A *Schizosaccharomyces pombe* gene coding for an activating product that acts on the expression of the thiamine-regulable genes under educing conditions (in the absence of thiamine) has also been found. The amplification of this gene, in particular by introduction into a multicopy vector—and transformation of a *Schizosaccharomyces pombe* strain which also comprises a large number of copies of a DNA fragment coding for a protein of interest, placed under the control of a thiamine-regulable promoter region, might enable the levels of production of the protein of interest to be improved in accordance with the culture conditions, especially in the absence of thiamine.

Traditionally, thiamine is added to yeast culture media. Its omission represents a lower cost and has little or no effect on their viability. These different criteria, which satisfy the conditions of production on an industrial scale, illustrate the advantages of the present invention.

Consequently, the subject of the present invention is the combined use, for the purpose of production of a protein of interest, of (a) a first expression cassette containing a first DNA fragment coding for said protein of interest, placed under the control of the elements necessary for its expression; said elements comprising, in particular, a first thiamine-regulable promoter region; and (b) a second expression cassette containing a second DNA fragment coding for a product that activates the thiamine-regulable genes, placed under the control of the elements necessary for its expression which comprise a second promoter region; said second expression cassette being inserted (i) into a multicopy vector or (ii) into the cell genome, and in case (ii) characterized in that said second promoter region is heterologous to said DNA fragment coding for said activating product.

As stated above, the present invention applied to the thiamine-regulated production of a protein of interest in a eukaryotic cell, in particular a Schizosaccharomyces strain, and most especially a strain of the species pombe.

For the purposes of the present invention, the first DNA fragment can originate from a eukaryotic or prokaryotic organism or from a virus. It may be isolated by any technique in use in the field of the art, for example by cloning, PCR (polymerase chain reaction) or chemical synthesis. Moreover, it may code for (i) an intracellular protein of interest, (ii) a membrane protein of interest present at the surface of the host yeast or (iii) a protein of interest secreted into the culture medium. It may hence comprise suitable additional elements such as, for example, a sequence coding for a secretion signal. Such elements are known to a person skilled in the art.

Moreover, the first DNA fragment may code for a protein of interest corresponding to all or part of a native protein as is found in nature. The encoded protein may also be a chimeric protein, for example one originating from the fusion of polypeptides of diverse origins, or from a mutant displaying improved and/or modified biological properties. Such a mutant may be obtained by molecular biology techniques. Among proteins of interest for the purposes of the present invention, the following may be mentioned more especially:

cytokines, and in particular interleukins, interferons, colony stimulating factors (CSF) and growth factors;

anticoagulants, preferably hirudin, in particular the hirudin variants described in European Application EP 332,523 and most especially the variant HV2 Lys 47;

enzymes such as trypsin and ribonucleases;

enzyme inhibitors such as α1-antitrypsin, antithrombin III and viral protease inhibitors;

the proteins involved in ion channels, such as the CFTR protein whose sequence is described in Riordan et al. (1989, Science, 245, 1066–1073);

proteins capable of inhibiting the initiation or progression of cancers, such as the expression products of tumor-suppressing genes, for example the p53 and Rb genes; and proteins capable of inhibiting a viral infection or its development, for example the antigenic epitopes of these viruses or altered variants of viral proteins capable of competing with the native viral proteins.

Naturally, these examples are not limiting.

Generally speaking, a promoter region which is functional in the cell in question and is thiamine-regulable will be employed for the expression of the first DNA fragment. This promoter region is isolated from the 5' flanking region of the thiamine-regulable genes such as the ones mentioned above. Naturally, it may be modified by mutation, deletion and/or addition of one or more nucleotide(s) with respect to the native promoter region, provided that these modifications do not drastically impair its capacity for regulation. Generally speaking, all or part of such a promoter region may be used in the context of the present invention. Thus, a promoter region of a thiamine-regulable gene, comprising a regulatory region capable of conferring regulation by thiamine and a TATA box homologous with said regulable gene, may be employed.

According to another embodiment, it is possible to employ a regulatory region originating from a thiamine-regulable gene, placed upstream of a minimal promoter region comprising a TATA box of any origin, capable of providing for a correct initiation of transcription of a first DNA fragment in the cell in question. A person skilled in the art is acquainted with such minimal promoter regions. Those of the *Schizosaccharomyces pombe* adh and CMV (cytomegalovirus) IE1 genes may be mentioned as examples (Boshart et al., 1985, Cell, 41, 521–530).

"Regulatory region" refers to a nucleotide sequence of variable size, capable of conferring regulation by thiamine, that is to say of inducing in the absence of thiamine an expression of the DNA fragment placed under its control at a level significantly higher than in the presence of thiamine. A regulatory region comprises, in particular, one or more activating and/or repressing elements responsible for regulation.

Although a single regulatory region is sufficient to provide for a regulation by thiamine, it is also possible to envisage employing several regulatory regions in tandem in order to increase the levels of expression. According to a use according to the present invention, from 1 to 25 regulatory regions, advantageously from 1 to 7 and preferably from 1 to 4, may be employed in particular. Moreover, the regulatory region or regions may be inserted upstream of a minimal promoter region in a sense or reverse orientation with respect to the TATA box. Preferably, this regulatory region is placed immediately upstream of the TATA box, that is to say at a distance of 1 to 35 bp, advantageously 1 to 20 bp, preferably 1 to 10 bp and as an absolute preference 1 to 6 bp.

It is most especially preferable to employ promoter regions originating from the *Schizosaccharomyces pombe* nmt1 or pho4 gene.

In the context of the present invention, a first promoter region originating from the *Schizosaccharomyces pombe* pho4 gene will preferably be employed. In this context, the inventors have characterized a regulatory region of 40 bp localized immediately upstream of the TATA box. Thus, according to an advantageous embodiment, a regulatory region in use in the present invention comprises at least 17 nucleotides of the sequence as shown in the sequence identifier NO:2, and beginning at the nucleotide at position +603 and ending at the nucleotide at position +642. The present invention also includes any sequence capable of hybridizing under stringent conditions with such a sequence, as well as its complementary sequence. Naturally, a regulatory region for the purposes of the invention may be larger and may comprise more sequence from the promoter region of the pho4 gene.

As nonlimiting examples, it is possible to envisage employing a regulatory region having a sequence as shown in the sequence identifier NO:2, beginning at the nucleotide at position +603 and ending at the nucleotide at position +642;

beginning at the nucleotide at position +593 and ending at the nucleotide at position +642;

beginning at the nucleotide at position +544 and ending at the nucleotide at position +642;

beginning at the nucleotide at position +496 and ending at the nucleotide at position +642;

beginning at the nucleotide at position +444 and ending at the nucleotide at position +642;

beginning at the nucleotide at position +255 and ending at the nucleotide at position +642; or beginning at the nucleotide at position +1 and ending at the nucleotide at position +642.

An especially advantageous construction is that which combines a regulatory region originating from the *Schizosaccharomyces pombe* pho4 gene and a minimal promoter region originating from the *Schizosaccharomyces pombe* adh gene. The latter region corresponds to the sequence as published in Russel et al. (1983, supra) and included between the nucleotides −119 and −12. It is self-evident that it may contain modifications (mutation, deletion and/or addition of one or more nucleotides) with respect to the published sequence, provided these modifications do not drastically reduce its capacity to initiate transcription.

Moreover, a first expression cassette in use in the present invention may, in addition, contain other elements contributing to the expression of the first DNA fragment, in particular a transcription termination sequence such as that of the *Schizosaccharomyces pombe* arg3 gene (Van Huffel et al., 1992, Eur. J. Biochem., 205, 33–43), as well as a transcription enhancer which is functional in the cell in question, for example the enhancer of the CMV IE1 gene.

A second expression cassette in use in the present invention codes for an activating product capable of activating the expression of a first DNA fragment placed under the control of a thiamine-regulable promoter region. The term "activating product" denotes a polypeptide capable of interacting either directly with the regulatory region involved in the regulation by thiamine, or indirectly via cell factors. The activating product is preferably one that acts at transcriptional level. Different genes or portions of genes isolated from a variety of eukaryotic cells and coding for a product that activates the expression of the thiamine-regulable genes may be used in the context of the present invention. Such activating genes may be obtained by any conventional technique in the field of the art, and in particular according to the technique described in Example 2, by complementation of a mutant cell displaying an absence of derepression of the expression of the genes normally induced in the absence of thiamine.

However, it is most especially preferable to employ a gene originating from *Schizosaccharomyces pombe*, coding for an activating product having the sequence as shown in the sequence identifier NO:1 beginning at the amino acid at position +1 and ending at the amino acid at position +775, or a functional variant of said activating product. "Functional variant" is understood to mean a polypeptide capable of exerting an activating function on the expression of the thiamine-regulable genes. Such functional variants may be obtained by mutation, deletion, substitution and/or addition of one or more amino acid residues. These modifications may be carried out according to the standard techniques of molecular biology. The functionality of the variant thereby obtained may be confirmed according to the technique described in Example 2, by transformation of the DNA fragments coding for each of these variants into mutant strains and measuring the derepression by restoration of a suitable enzyme activity.

A use according to the present invention comprises the case where the second expression cassette is included in an autonomously replicating vector and, in this case, the second DNA fragment may be under the control either of its own promoter region or of a second promoter region heterologous to said DNA fragment. According to another variant, the second expression cassette is inserted into the genome of the host cell, provided that the second DNA fragment is placed under the control of a second promoter region heterologous to said DNA fragment.

As regards a second heterologous promoter region, this may be constitutive or regulable and of any origin provided that it is functional in the host cell. The choice of such a promoter region is within the capacity of a person skilled in the art. The promoter regions of the *Schizosaccharomyces pombe* adh and fbp genes and of the CMV IE1 gene may nevertheless be mentioned.

However, it can be advantageous to use a second thiamine-regulable promoter region of the same type as the first promoter region in use in the present invention.

As before, the second expression cassette may contain other elements necessary for the expression of the second DNA fragment, such as the ones mentioned above.

According to the variant which is, moreover, preferred, in which one or more copy(ies) of the second expression cassette is/are inserted into an expression vector, a multicopy expression vector is employed in particular, and especially a vector comprising one or more copy(ies) of the first expression cassette. The insertion of the second expression cassette in use in the present invention is preferably carried out outside the actual first expression cassette. Such a vector may contain, moreover, elements providing for its replication, that is to say an origin of replication such as the *Schizosaccharomyces pombe* ars1 origin, and optionally the *Escherichia coli* ori origin. In addition, it may also comprise selectable genes such as the *Saccharomyces cerevisiae* URA3 or LEU2 gene, the *Schizosaccharomyces pombe* ura4 or leu1 gene or an antibiotic resistance gene. It is most especially preferable to employ a multicopy vector present at between 20 and 500 copies in the host cell, advantageously between 25 and 400 copies and preferably between 50 and 300 copies.

In the context of the present invention, the first and second expression cassettes are present in a host cell according to a copy number ratio of 200:1, advantageously 25:1, preferably 10:1 and as an absolute preference 1:1.

The present invention also extends to the host cells in which a use according to the present invention is employed, and especially to yeasts selected from the following strains: *Schizosaccharomyces pombe, Schizosaccharomyces sloofiae, Schizosaccharomyces malidevorans, Schizosaccharomyces octosporus* and *Hasegawaea japonicus*. A large number of these strains are commercially available in bodies such as the AFRC (Agriculture and Food Research Council, Norfolk, UK) or the ATCC (Rockville, Mass., USA).

The present invention also relates to a third expression cassette comprising a DNA fragment coding for a protein of interest, placed under the control of the elements necessary for its expression, said elements containing a thiamine-regulable promoter region originating from the *Schizosaccharomyces pombe* pho4 gene. Such a promoter region is defined above.

The present invention also extends to:
(i) an expression vector comprising a third expression cassette according to the invention; and
(ii) a host cell comprising a third expression cassette or an expression vector according to the invention. A yeast cell advantageously of the genus Schizosaccharomyces and preferably of the species pombe is most especially preferred.

Lastly, the present invention also relates to a method for the production of a protein of interest by a host cell according to the invention, in particular a *Schizosaccharomyces pombe* cell, according to which:
said host cell is cultured in a suitable medium in the absence of thiamine; and
said protein of interest is recovered.

In the context of the invention, the protein of interest may be recovered directly in the culture medium or after lysis of the cells according to conventional techniques. Moreover, it may be purified by applying the standard techniques known to a person skilled in the art, for example and as a guide, by chromatography or immuno-purification.

The examples below will enable other features and advantages of the present invention to be brought out. These examples are illustrated by reference to the following figures:

FIG. 1 is a diagrammatic representation of the cassettes for the expression of the DNA fragment coding for HV2 Lys 47, placed under the control of a thiamine-regulable promoter region (pTG2734 and pTG2735), constitutive (pTG1757) or nonfunctional (pTG1758).

FIG. 2 is a diagrammatic representation of an expression vector containing a first cassette for the expression of the Lys 47 variant of hirudin (HV2) under the control of the pho4 promoter and an activating gene (ACT) capable of activating the pho4 promoter, as well as an origin of replication (ars) and genes coding for selectable markers (amp and selection).

FIG. 3 is a diagrammatic representation of the vectors for deletion of the regulatory region (UAS) of the pho4 gene (pTG4734 to pTG4738) and the control vectors (pTG2735: complete pho4 regulatory region; pTG1758: adh minimal promoter region; and pTG4766: adh minimal promoter region supplemented with 30 bp of 5' sequence and with a SalI site). The capacity of these vectors to produce and secrete hirudin (HV2) after culture in a medium lacking or containing thiamine (−thi or +thi) is shown in abbreviated form (+or −).

The constructions described below are carried out according to the general techniques of genetic engineering and molecular cloning detailed in Maniatis et al. (1989, Laboratory Manual, Cold Spring Harbor Laboratory Press, Cold Spring Harbor, N.Y.). All of the cloning steps employing bacterial plasmids are performed by transfer into *E. coli* strain 5K.

To introduce the different vectors into the *Schizosaccharomyces pombe* strains, the lithium acetate technique (Ito et al., 1983, J. Bacteriol., 153, 163–168) is used. However, any other standard technique may be employed.

EXAMPLE 1

Construction of expression vectors in which the gene coding for the variant HV2 Lys 47 is placed under the control of a promoter region derived from the *Schizosaccharomyces pombe* pho4 gene A. Vector pTG2734 in which the HV2 Lys 47 gene is placed under the control of the promoter region isolated from the Schizosaccharomyces pombe pho4 gene The plasmid pEVp11 (Russell and Nurse, 1986, Cell, 45, 145–153) contains the promoter region of the *Schizosaccharomyces pombe* adh gene in the form of a 700-bp SphI-EcoRI fragment, the EcoRI site being located in the 5' region of the adh gene 59 bp upstream of the initiation ATG. It is digested with the enzymes EcoRI and HindIII, and a synthetic fragment resulting from the recombination of the single-stranded oligonucleotides OTG2781 and OTG2782 (described, respectively, in SEQ ID NO:3 and NO:4) is introduced with the object of supplementing the adh promoter region up to 11 bp upstream of the initiation ATG and of creating suitable restriction sites facilitating the subsequent cloning steps. pTG1702 is generated, into which a sequence coding for the secretion signal of *Schizosaccharomyces pombe* major acid phosphatase (pho 1) is inserted downstream of the adh promoter region. For this purpose, a synthetic DNA fragment originating from the recombination of the oligonucleotides OTG2872 and OTG2873 (SEQ ID NO: 5 and NO:6) is ligated to pTG1702 previously digested with BamHI and SacI. pTG1716 is obtained.

The latter is modified by the insertion of a DNA sequence coding for the Lys 47 variant of hirudin (HV2 Lys47). pTG1716 is digested with MluI and HindIII before being ligated, on the one hand to a synthetic fragment possessing MluI and AccI protruding ends and resulting from the recombination of the oligonucleotides OTG2874 and OTG2875 (described, respectively, in SEQ ID NO:7 and NO:8), and on the other hand to an AccI-HindIII fragment isolated from the vector pTG2974. The latter carries, in particular, a DNA fragment coding for HV2 Lys 47.

The expression cassette is supplemented by the introduction, at the 3' end of the HV2 Lys 47 gene, of a transcription termination sequence corresponding to the 3' region of the *Schizosaccharomyces pombe* arg3 gene. A 0.92-kb HpaI-ClaI fragment is isolated from pCVH3 (Van Huffel et al., 1992, Eur J. Biochem., 205, 33–43) and then treated with the Klenow fragment of DNA polymerase. This fragment contains the last codons of the *Schizosaccharomyces pombe* arg3 gene, followed by the transcription termination sequence. It is inserted into pTG1702 digested with HindIII and whose ends have been blunted by treatment with the Klenow fragment of DNA polymerase, to give pTG1746.

pTG1746 is digested with XbaI and treated with the Klenow fragment of DNA polymerase before being digested with BamHI. The fragment containing the transcription termination sequences is introduced into the vector pDW230 digested with EcoRI, subjected to a treatment with the Klenow fragment of DNA polymerase and then digested with BamHI. pTG1751 is obtained.

The vector pDW230 is similar to pDW232 described in the literature (Weilguny et al., 1991, Gene, 99, 47–54). They are both derived from pGEM3 into which an origin of replication which is functional in *Schizosaccharomyces pombe* (ars1 origin), and also the Schizosaccharomyces pombe ura4 gene as selectable marker, have been inserted; except for the fact that the introduction of the fragment carrying the ars1 origin at the NaeI site of pGEM3, giving rise to pDW230, has brought about a deletion of this site up to base 2862.

The SphI-SacI fragment containing the adh promoter region followed by the sequence coding for the pho1 secretion signal and HV2 Lys 47 is isolated from pTG1722. It is then subcloned between the same sites as pTG1751. This results in pTG1757, in which the expression of HV2 Lys 47 is controlled by the adh promoter region and is hence constitutive (FIG. 1).

In addition, the promoter region of the *Schizosaccharomyces pombe* pho4 gene is obtained by PCR (polymerase chain reaction) from the clone pSp4B (Yang and Schweingruber, 1990, Current Genet., 18, 269–272) and using the primers OTG3569 containing an SphI site (SEQ ID NO:9) and OTG3239 equipped with a BamHI site (SEQ ID NO:10).

The SphI-BamHI fragment thus generated is substituted for the SphI-BamHI fragment carrying the adh promoter region of pTG1757 to give pTG2734 (FIG. 1).

B. Construction of vectors for the expression of HV2 Lys 47 comprising a “pho4-adh” hybrid promoter region and characterization of the regions of the pho4 gene involved in regulation by thiamine A 642-bp fragment containing the 5' flanking sequences of the *Schizosaccharomyces pombe* pho4 gene located upstream of the TATA box is isolated by PCR and from the vector pTG2734. The primers OTG3569 (SEQ ID NO:9) and OTG3210 (SEQ ID NO:11) are employed.

The SphI-NcoI PCR fragment thus obtained is introduced into pTG1757 digested with the same enzymes to give pTG2735 (FIG. 1).

In order to localize the regulatory regions of the pho4 gene which are responsible for regulation by thiamine, a number of PCR fragments were generated from pTG2734, and from the primer OTG3210 described above combined with one of the following primers (see Table 1):

TABLE 1

| Primer | Expression vector | Size of the synthesized pho4 5' region |
|---|---|---|
| OTG4645 (SEQ ID NO: 12) | pTG4734 | 50 bp |
| OTG4646 (SEQ ID NO: 13) | pTG4735 | 99 bp |
| OTG4647 (SEQ ID NO: 14) | pTG4736 | 147 bp |
| OTG4648 (SEQ ID NO: 15) | pTG4737 | 199 bp |
| OTG4649 (SEQ ID NO: 16) | pTG4738 | 388 bp |

Each of the SphI-NcoI PCR fragments generated is subcloned as above into the vector pTG1757 treated with the same enzymes. A diagrammatic representation of these fragments forms the subject of FIG. 3.

Lastly, the vector pTG5701 is generated by introduction into pTG1757 of a DNA fragment equipped with SphI and NcoI ends and originating from the recombination of the oligonucleotides OTG4924 and OTG4925 (SEQ ID NO: 17 and 18). Thus, in pTG5701, the expression of HV2 Lys 47 is placed under the control of a 40-bp regulatory region of the pho4 gene preceding the TATA box of the adh gene.

C. Construction of a vector for the expression of HV2 Lys 47 comprising a "pho4-adh" hybrid promoter region and in which the pho4 regulatory region is in the antisense orientation with respect to the TATA box of the adh gene The vector pTG4734 is digested with SphI and NcoI, then treated with T4 DNA polymerase and then religated. The clones containing a copy of a 50-bp regulatory region of the pho4 gene but in the reverse orientation with respect to the vector of origin pTG4734, and hence to the TATA box of the adh gene, are verified by sequencing according to traditional methods.

D. Construction of vectors for the expression of HV2 Lys 47 comprising a "pho4-adh" hybrid promoter region including several 50-bp pho4 regulatory regions in tandem.

A DNA fragment corresponding to a 50-bp regulatory region of the pho4 gene equipped at both of its ends with a BglII restriction site is generated by recombination of the oligonucleotides OTG5296 and OTG5297 (SEQ ID NO: 19 and 20). The step of rehybridization of the two oligonucleotides is followed by a ligation step and then by a treatment with T4 DNA polymerase. The reaction mixture is then ligated to the vector pTG1757 (as a replacement for the corresponding fragment) digested beforehand with SphI and NcoI and treated with T4 DNA polymerase.

The number of 50-bp "units" from pho4 and also their orientation are verified by sequencing in the clones obtained. In this way, pTG8607, pTG8608 and pTG8609, comprising 1, 2 and 3 copies, respectively, of 50-bp regulatory region in the antisense orientation with respect to the TATA box of the adh gene, are generated.

EXAMPLE 2

Construction of vectors for the expression of the HV2 Lys 47 gene containing, in addition, the activating gene of Schizosaccharomyces pombe A. Cloning of the activating gene of Schizosaccharomyces pombe The gene coding for an activating product capable of activating the expression of the thiamine-regulable genes is isolated by complementation from a mutant strain, of Schizosaccharomyces pombe displaying an absence of derepression of the expression of the pho4 gene in the absence of thiamine. Genomic fragments partially digested with Sau3A are isolated from a wild-type Schizosaccharomyces pombe strain. They are cloned into the BamHI site of the vector pUR19 (Barbet et al., 1992, Gene, 114, 59–66) and then introduced into the mutant strain thi1-23 ura4 D18 pho1-44 (Schweingruber et al., 1992, Genetics, 130, 445–449).

The transformants are selected for prototrophy for uracil and 5-(2-hydroxyethyl)-4-methylthiazole (Zurlinden and Schweingruber, 1992, Gene, 117, 141–143). 14 transformants are obtained and their plasmid DNA is isolated according to the protocol described in Moreno et al. (1991), Methods in Enzymology, 194, 795–823). The DNA is then amplified in *Escherichia coli* according to standard methods (Maniatis et al., 1982, Molecular cloning: a laboratory manual, Cold Spring Harbor Laboratory, Cold Spring Harbor, N.Y.). Four transformants possess a 4-kb insert which, after transformation into the above mutant strain, is capable of abolishing the absence of derepression. This manifests itself in the restoration of an acid phosphatase activity in a medium lacking thiamine, measured according to the technique described in Schweingruber et al. (1986, J. Biol. Chem., 261, 15877–15882). Hence it is probable that the 4-kb insert comprises a gene that activates the expression of the thiamine-regulable genes nmt1 and pho4.

The sequence of the majority of the insert is determined according to conventional techniques known to a person skilled in the art. The data enable an open reading frame of 775 residues, whose sequence is reported in the sequence identifier NO:1 (SEQ ID NO:1), to be demonstrated.

Figure 2:
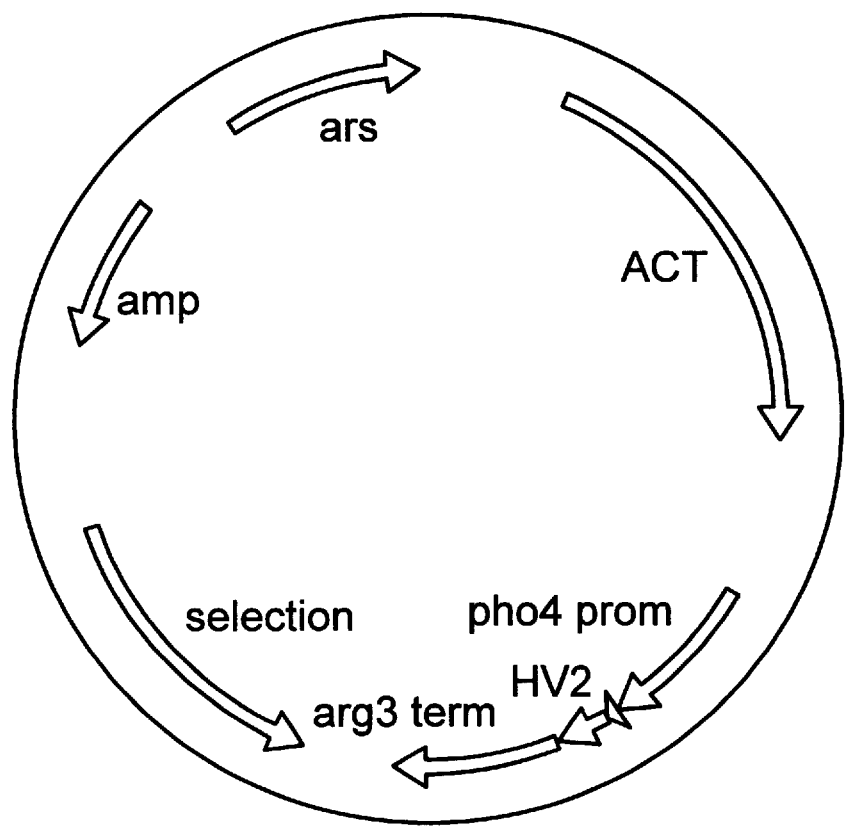

B. Combined use of the activating gene of *Schizosaccharomyces pombe* and of a cassette for the expression of HV2 Lys 47 under the control of a promoter region originating from the pho4 gene SphI-EcoRI fragment is isolated from the plasmid pUR19 comprising the 4-kb insert and treated with the T4 DNA polymerase before being introduced into Schizosaccharomyces multicopy replicative expression vectors containing an expression cassette controlled by the pho4 promoter and suitable selectable markers. A vector of this type is shown in FIG. 2.

C. Combined use of the activating gene of *Schizosaccharomyces pombe* and a cassette for the expression of HV2 Lys 47 under the control of a promoter region originating from the nmt1 gene A 188-bp PCR fragment is generated from the genomic DNA isolated from a *Schizosaccharomyces pombe* strain by conventional techniques. The oligonucleotides OTG5217 and OTG3028 (described in SEQ ID NO: 21 and 22, respectively) are used. The SphI and BamHI fragment thus generated is introduced between the same sites of the vector pTG1757. The vector pTG5774 is obtained.

The DNA fragment coding for the activating product is inserted into a Schizosacccharomyces multicopy replicative vector containing, in particular, an expression cassette controlled by the nmt1 promoter.

EXAMPLE 3

Production of HV2 Lys 47 in accordance with the plasmid used

The expression vectors of Examples 1 and 2 are introduced into a Schizosaccharomyces strain, and the level of expression of the DNA fragment encoding hirudin is evaluated according to the methodology described below.

A *Schizosaccharomyces pombe* strain, for example the strain D18 available at the AFRC under the reference 2036, is transformed with the expression vectors mentioned above. The same strain transformed in parallel with the vector pTG1758 (FIG. 1), containing a truncated promoter region reduced to the minimal promoter region of the adh gene, is used as a negative control. The positive control of expression consists of pTG1757 permitting a constitutive expression of HV2 Lys 47 under the control of the promoter region of the adh gene.

The transformed strains are cultured in Kappeli medium supplemented with 2% of glucose and a mixture of vitamins comprising, in particular, thiamine at a final concentration of 0.002 g/l (thi+medium). When the cultures reach an OD (optical density) at 600 nm of between 1 and 2, they are diluted to an OD of approximately 0.05, either in thi+ medium of composition as stated above, or in Kappeli medium supplemented with 2% of glucose and a mixture of vitamins lacking thiamine (thi−medium). Culture aliquots are sampled regularly during the exponential growth phase and also at the end of growth (OD 600 nm between 7 and 9).

For each sample removed, the amount of hirudin secreted into the culture medium is determined. Although it is possible to assay hirudin by all conventional techniques, the ELISA technique as described in Koch et al. (1993, Analytical Biochemistry, 214, 301–312), employing the pair of monoclonal antibodies MATG102 and MATG106 and hirudin titrated as described in the above-mentioned reference, is used. Moreover, the level of expression of hirudin may also be evaluated by Northern analysis of the mRNAs isolated from the *Schizosaccharomyces pombe* cells. A probe capable of hybridizing specifically with the sequences coding for HV2 Lys 47, for example a probe originating from the AccI-SacI fragment of pTG1757, is employed. However, other probes, such as oligonucleotides, may be employed.

Figure 3:
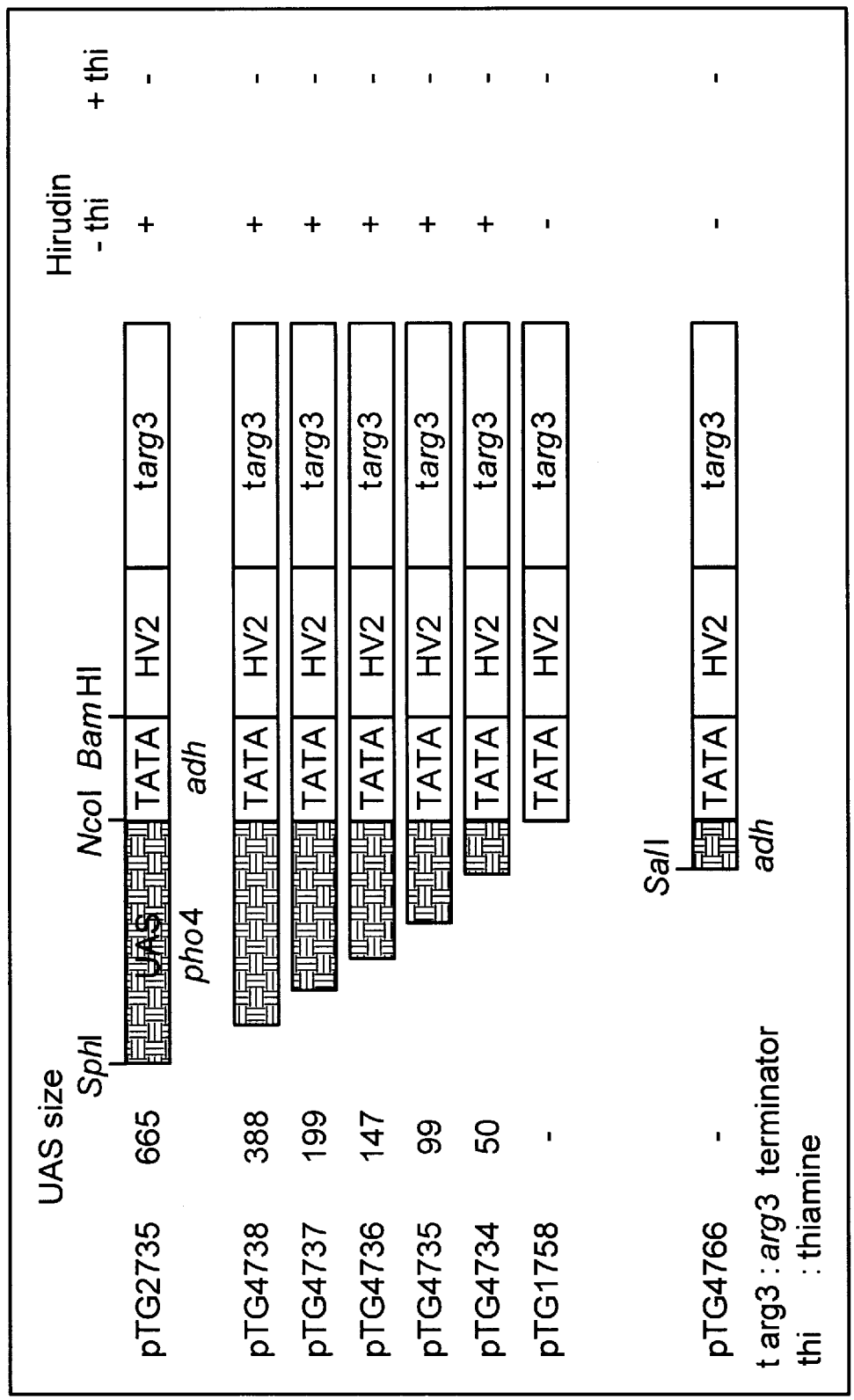

Table 2 summarizes the levels of hirudin secreted by *Schizosaccharomyces pombe* transformed with each of the plasmids indicated, and according to whether the culture medium does or does not contain thiamine (thi+or thi−) (see also FIG. 3).

TABLE 2

| Vector | pho4 5' region | Orientation | TATA box | Level of HV2 Lys 47 | |
|---|---|---|---|---|---|
| | | | | thi+ | thi− |
| pTG1757 | – | – | adh | +++ | +++ |
| pTG1758 | – | – | adh | – | – |
| pTG5701 | 40 bp | sense | adh | – | ++ to +++ |
| pTG4734 | 50 bp | sense | adh | – | +++ |
| pTG4735 | 99 bp | sense | adh | – | +++ |
| pTG4736 | 147 bp | sense | adh | – | +++ |
| pTG4737 | 199 bp | sense | adh | – | +++ |
| pTG4738 | 388 bp | sense | adh | – | ++ |
| pTG2735 | 642 bp | sense | adh | – | +++ |
| pTG2734 | 642 bp | sense | pho4 | – | +++ |
| pTG4770 | 50 bp | anti-sense | adh | – | +++ |

Estimates of the amount of HV2 Lys 47 mRNA by Northern blotting confirm these results.

Moreover, when the mRNAs present in the *Schizosaccharomyces pombe* cells transformed with pTG8607, pTG8608 or pTG8609 and cultured in the presence of thiamine are analyzed by Northern blotting, no hybridization signal can be detected. In contrast, when the cells are cultured in a medium lacking thiamine, a large increase in the amount of HV2 Lys 47 mRNA is observed. The intensity of the hybridization signal correlates with the number of copies of the 50-bp pho4 sequence.

These results collectively show that, in the presence of thiamine, the expression of the gene of interest is repressed, whereas, in its absence, a strong induction is observed, manifesting itself in the presence of a large amount of hirudin secreted into the culture medium.

Moreover, these experiments made it possible to identify a regulatory region which may be qualified as minimal, lying within the promoter region of the *Schizosaccharomyces pombe* pho4 gene and responsible for the regulation by thiamine. This region of 40 to 50 bp is located upstream of the TATA box and is sufficient on its own to confer such a regulation (repression in the presence of thiamine and derepression in the absence of thiamine). The fact that this region functions irrespective of its orientation with respect to the TATA box is unexpected.

Lastly, the presence of several copies of this minimal region upstream of a TATA box has a synergistic effect on the level of expression, which effect appears to correlate with the number of copies of this region.

EXAMPLE 4

Construction of a vector of the expression of the CFTR protein under the control of a "Pho4-adh" hybrid promoter region The vector pTG5960, originating from p poly III-I* (Lathe et al., Gene, 1987, 57, 193–201) and modified by the insertion of the sequence coding for the human CFTR protein whose amino acid sequence is disclosed in Riordan et al. (1989, supra), is digested with the enzymes AvaI and XhoI. The AvaI-XhoI fragment comprising the nucleotide sequence coding for the CFTR protein is treated with the large Klenow fragment of DNA polymerase and inserted into the *Schizosaccharomyces pombe* expression vector pTG2735 digested with SacI and BamHI and treated with T4 DNA polymerase. pTG5999 is generated.

The AvaI-XhoI-Klenow fragment is introduced in parallel into the vector pTG1702 digested with BamHI and treated with the large Klenow fragment of DNA polymerase to give pTG1753 (constitutive expression of the CFTR gene under the control of the promoter region of the *Schizosaccharomyces pombe* adh gene).

After transformation of *Schizosaccharomyces pombe* D18 with pTG1753, no transformant produces CFTR protein. Analysis by restriction mapping shows that the plasmids isolated from the transformants are rearranged, for example at the FTR sequence. These results indicate that the expression of the CFTR protein is probably toxic for the cells.

After introduction of pTG5999 into *Schizosaccharomyces pombe* strain D18 according to the protocol described above, the transformants are cultured in the presence or absence of thiamine. Cell aliquots are removed as culturing proceeds and the production of the CFTR protein is determined by Western blotting (Dalemans et al., 1992, Experimental Cell Research, 201, 235–240). No signal is seen in the cultures placed in a thi+medium (repression of the expression due to the presence of thiamine), whereas a band having the expected molecular mass is detected in the cultures set up in the absence of thiamine.

These results show the usefulness of the promoter region originating from the pho4 gene for the production of toxic proteins.

EXAMPLE 5

Influence of the position of the 50-bp region of the pho4 gene responsible for regulation by thiamine with respect to the TATA box.

In order to determine whether nearness of this region to the TATA box is required for the functions of activation and of repression, it was cloned at two other positions more distant from the adh TATA box.

The plasmid pTG6726 is obtained by digestion of pTG4734 with the restriction enzyme NcoI, treatment with phage T4 DNA polymerase and ligation. Under these conditions, the pho4 50-bp unit is separated by 10 bp from the TATA box of the adh gene.

The vector pTG5786 originates from the cloning of the SphI-NcoI fragment isolated from pTG4734 and carrying the pho4 50-bp unit into the SalI site of pTG4766 after treatment with T4 DNA polymerase. As a result, after ligation, the distance separating the 50-bp unit from the adh TATA box is 40 pb. The plasmid pTG4766 is derived from pTG1757 by introduction of a 30-pb Sate site up-stream of the adh TATA box. This modification has no effect on the activity of the adh promoter, and the deletion of the sequences located upstream of the SalI site (as produced in pTG4766) inhibits the promoter activity (behavior comparable to pTG1758).

Lastly, the vector pTG5787 was constructed in a similar manner, except for the fact that the pho4 50-bp unit is cloned in the reverse orientation. In this case, the distance from the TATA box is 36 bp.

Plasmids pTG6729, pTG5786 and pTG5787 were introduced into D18 yeast. After culture in the presence or absence of thiamine, the transcripts synthesized by these different transformants were analyzed by Northern blotting. The amount of transcripts present in the strain transformed with pTG6729 in the absence of thiamine is less than that obtained with the strain carrying plasmid pTG4734, but in the presence of thiamine the repression is preserved. As regards the strains transformed with plasmids pTG5786 and pTG5787, the efficiency of transcription is comparable irrespective of the culture conditions (plus or minus thiamine), and it is similar to that measured in the strain carrying pTG4734 in the absence of thiamine.

Thus, the distancing of the 50-bp unit by 10 bp with respect to the adh TATA box decreases its capacity to activate transcription, but does not modify the repression by thiamine. In contrast, when the unit is at a distance of 40 bp from the TATA box, its activating properties remain intact but it becomes incapable of repressing transcription.

It is apparent that nearness between the 50-bp regulatory region of the pho4 gene and the TATA box is necessary in order for the repression by thiamine to be effective.

We claim:

1. Expression cassettes for the production of a protein of interest, comprising
    (a) a first expression cassette containing a first DNA fragment coding for said protein of interest, placed under the control of elements necessary for its expression; said elements comprising a first thiamine-regulable promoter region; and
    (b) a second expression cassette containing a second DNA fragment coding for a product that activates thiamine-regulable genes, placed under control of the elements necessary for its expression which comprises a second promoter region; said second expression cassette being inserted (i) into a multicopy vector or (ii) into the cell genome, and in case (ii) wherein said second promoter region is heterologous to said DNA fragment coding for said activating product.

2. Expression cassettes according to claim 1, wherein said first expression cassette and said second expression cassette are present according to copy number ratio of 200:1.

3. Expression cassettes according to claim 1, wherein the second DNA fragment codes for an activating product having the sequence shown in the sequence identifier NO:1 beginning at the amino acid at position +1 and ending at the amino acid at position +775, or a functional variant of said activating product.

4. Expression cassettes according to claim 3, wherein said second promoter region is heterologous to said DNA fragment coding for said activating product and is regulable by thiamine.

5. Expression cassettes according to claim 4, wherein the first and/or second thiamine-regulable promoter regions originate from genes selected from the group consisting of the *Schizosaccharomyces pombe* pho 4 and nmt1 genes.

6. Expression cassettes according to claim 5, wherein the first and/or second thiamine-regulable promoter regions originate from the *Schizosaccharomyces pombe* pho4 gene.

7. Expression cassettes according to claim 4, wherein the first and/or second thiamine-regulable promoter regions comprise at least one regulatory region conferring regulation by thiamine, said regulatory region being placed upstream of a minimal promoter region.

8. Expression cassettes according to claim 7, wherein said regulatory region is placed immediately upstream of the TATA box of a minimal promoter region.

9. Expression cassettes according to claim 7, wherein the first and/or second thiamine-regulable promoter regions comprise from 1 to 25 regulatory regions.

10. Expression cassettes according to claim 7, wherein the regulatory region or regions is/are in a sense or antisense orientation with respect to said minimal promoter region.

11. Expression cassettes according to claim 7, wherein the regulatory region of regions originate(s) from the *Schizosaccharomyces pombe* pho4 gene.

12. Expression cassettes according to claim 11, wherein the regulatory region comprises at least 17 contiguous nucleotides of a sequence as shown in the sequence identifier NO:2 beginning at the nucleotide at position +617 and ending at the nucleotide at position +642.

13. Expression cassettes according to claim 12, wherein the regulatory region is the sequence as shown in the sequence identifier NO:2
   beginning at the nucleotide at position +603 and ending at the nucleotide at position +642;
   beginning at the nucleotide at position +593 and ending at the nucleotide at position +642;
   beginning at the nucleotide at position +544 and ending at the nucleotide at position +642;
   beginning at the nucleotide at position +496 and ending at the nucleotide at position +642;
   beginning at the nucleotide at position +444 and ending at the nucleotide at position +642;
   beginning at the nucleotide at position +255 and ending at the nucleotide at position +642; or
   beginning at the nucleotide at position +1 and ending at the nucleotide at position +642.

14. Expression cassettes according to claim 7, wherein the minimal promoter region originates from the *Schizosaccharomyces* pombe adh gene.

15. Expression cassettes according to claim 1, wherein said second expression cassette is inserted into a multicopy expression vector.

16. Expression cassettes according to claim 15, wherein said multicopy expression vector comprises more than one copy of said first expression cassette.

17. Expression cassettes according to claim 1, wherein at least one copy of said second expression cassette is inserted into the genome of a host cell, said host cell comprising at least one copy of said first expression cassette, inserted either into the genome of the host cell or into a multicopy vector.

18. A host cell comprising a first cassette and a second cassette as are defined in claim 1.

19. A host cell according to claim 18, wherein said host cell is selected from the group consisting of *Schizosaccharomyces pombe, Schizosaccharomyces sloofiae, Schizosaccharomyces malidevorans, Schizosaccharomyces octosporus* and *Hasegawaea japonicus*.

20. A method for the production of a protein of interest by a host cell according to claim 18, wherein:
   said host cell is cultured in a thiamine-free medium; and
   said protein of interest is recovered.

21. A method for the production of a protein of interest according to claim 20, wherein said host cell is a *Schizosaccharomyces probe* strain.

22. An expression cassette comprising a DNA fragment coding for a protein of interest, placed under the control of elements necessary for its expression, said elements containing a thiamine-regulable promoter region originating from *Schizosaccharomyces pombe* pho4 gene.

23. An expression vector comprising an expression cassette according to claim 22.

24. A host cell comprising an expression cassette according to claim 22.

25. A method for the production of a protein of interest by a host cell according to claim 24, wherein
   said host cell is cultured in a thiamine-free medium, and
   said protein of interest is recovered.

26. A method for the production of a protein of interest according to claim 25, wherein said host cell is a *Schizosaccharomyces pombe* strain.

27. An expression cassette according to claim 22, wherein said thiamine-regulable promoter region comprises at least one regulatory region conferring regulation by thiamine, said regulatory region being placed upstream of a minimal promoter region.

28. An expression cassette according to claim 27, wherein said regulatory region is placed immediately upstream of the TATA box of a minimal promoter region.

29. An expression cassette according to claim 27, wherein the thiamine-regulable promoter region comprises from 1 to 25 regulatory regions.

30. An expression cassette according to claim 27, wherein the regulatory region is in the same or the opposite orientation with respect to said minimal promoter region.

31. An expression cassette according to claim 27, wherein the regulatory region originates from the *Schizosaccharomyces pombe* pho4 gene.

32. An expression cassette according to claim 31, wherein the regulatory region comprises at least 17 contiguous nucleotides of a sequence as shown in the sequence identifier no. 2: beginning at the nucleotide at position +617 and ending at the nucleotide at position +642.

33. An expression cassette according to claim 32, wherein the regulatory region is the sequence as shown in the SEQ ID NO. 2:
   beginning at the nucleotide at position +603 and ending at the nucleotide at position +642;
   beginning at the nucleotide at position +593 and ending at the nucleotide at position +642;
   beginning at the nucleotide at position +544 and ending at the nucleotide at position +642;
   beginning at the nucleotide at position +496 and ending at the nucleotide at position +642;
   beginning at the nucleotide at position +444 and ending at the nucleotide at position +642;
   beginning at the nucleotide at position +255 and ending at the nucleotide at position +642; or
   beginning at the nucleotide at position +1 and ending at the nucleotide at position +642.

34. An expression cassette according to claim 27, wherein the minimal promoter region originates from the *Schizosaccharomyces probe* adh gene.

* * * * *

UNITED STATES PATENT AND TRADEMARK OFFICE
CERTIFICATE OF CORRECTION

PATENT NO. : 5,834,237
DATED : November 10, 1998
INVENTOR(S) : Jacobs et al.

It is certified that error appears in the above-identified patent and that said Letters Patent is hereby corrected as shown below:

On the title page, Item [75],

Please correct the spelling of the last named inventor, from "Ernst Schweinbryber" to --Ernst SCHWEINGRUBER--.

Signed and Sealed this

Eighteenth Day of May, 1999

Attest:

Q. TODD DICKINSON

*Attesting Officer*    *Acting Commissioner of Patents and Trademarks*

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 775 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v i ) ORIGINAL SOURCE:
        ( A ) ORGANISM: Schizosaccharomyces pombe ( x i ) SEQUENCE DESCRIPTION: SEQ ID NO:1:

```
Met Asn Glu Glu Ile Gly Phe Leu Lys Asn Gln Leu Phe Ala Asp Val
 1               5                  10                  15
Lys Asp Leu Glu Arg Lys Lys Lys Arg Arg Val Pro Pro Glu Gln Arg
            20                  25                  30
Arg Arg Val Phe Arg Ala Cys Lys His Cys Arg Gln Lys Lys Ile Lys
        35                  40                  45
Cys Asn Gly Gly Gln Pro Cys Ile Ser Cys Lys Thr Leu Asn Ile Glu
    50                  55                  60
Cys Val Tyr Ala Gln Lys Ser Gln Asn Lys Thr Leu Ser Arg Glu Tyr
65                  70                  75                  80
Leu Glu Glu Leu Ser Glu Arg Gln Leu Cys Leu Glu Tyr Ile Phe Ser
                85                  90                  95
Arg Met Cys Pro Asn Phe Asn Leu Glu Thr Lys Asn Leu Ile Ser Ile
            100                 105                 110
Ser Lys Lys Leu Ser Glu Asn Glu Asn Leu Pro Val Ser Lys Ile Ala
        115                 120                 125
Glu Val Thr Asn Glu Leu Asp Thr Leu Val Arg Ile Asn Asp Gln Leu
    130                 135                 140
```

```
Ser  Arg  Asn  His  Ile  Ser  Gly  Thr  Thr  Glu  Glu  Met  Gln  Ser  Ser  Ser
145                 150                      155                           160

Ser  Leu  Ile  Ala  Gly  Glu  Val  Gln  Pro  Gly  Ile  Ser  Phe  Arg  Asp  Gln
                165                      170                           175

Leu  Lys  Val  Gly  Lys  Leu  Glu  Asp  Thr  Leu  Tyr  Leu  Gly  Pro  Thr  Thr
                180                      185                      190

Ser  Glu  Ala  Phe  Ile  Glu  Arg  Leu  Gln  Asn  Glu  Leu  Glu  Leu  Glu  Ser
           195                      200                      205

Ile  Ser  Glu  Asp  Asp  Leu  Tyr  Ser  Lys  Arg  Leu  Ser  Pro  Ser  Val  Ser
     210                      215                      220

Tyr  Ser  Glu  Phe  Asp  Glu  Gln  Leu  Leu  Leu  His  Ala  Arg  Ser  Leu  Ile
225                      230                      235                           240

Pro  Ser  Lys  Ala  Val  Val  Glu  Phe  Leu  Ile  Asn  Ser  Phe  Phe  Ile  Asn
                245                      250                           255

Val  Gln  Thr  Asn  Leu  Phe  Val  Tyr  His  Pro  His  Phe  Phe  Lys  Cys  Arg
                260                      265                      270

Leu  Glu  Ile  Phe  Leu  Ala  Met  Glu  Asn  Gln  Ile  Asp  Ala  Gly  Phe  Leu
           275                      280                      285

Cys  Ile  Leu  Leu  Met  Val  Leu  Ala  Phe  Gly  Asn  Gln  Tyr  Thr  Ala  Glu
     290                      295                      300

Gln  Gln  Glu  Asp  Val  Ser  Lys  Ser  Asn  Phe  His  Ala  Ser  Asn  Ile  Gly
305                      310                      315                           320

Asn  Arg  Leu  Phe  Ser  Ala  Ala  Leu  Ser  Ile  Phe  Pro  Leu  Val  Leu  Leu
                325                      330                           335

Gln  Ser  Asp  Val  Ser  Ala  Val  Gln  Ser  Ser  Leu  Leu  Ile  Gly  Leu  Tyr
                340                      345                           350

Leu  Gln  Ser  Thr  Ile  Tyr  Glu  Lys  Ser  Ser  Phe  Ala  Tyr  Phe  Gly  Leu
           355                      360                      365

Ala  Ile  Lys  Phe  Ala  Val  Ala  Leu  Gly  Leu  His  Lys  Asn  Ser  Asp  Asp
     370                      375                      380

Pro  Ser  Leu  Thr  Gln  Asn  Ser  Lys  Glu  Leu  Arg  Asn  Arg  Leu  Leu  Trp
385                      390                      395                           400

Ser  Val  Phe  Cys  Ile  Asp  Arg  Phe  Val  Ser  Met  Thr  Thr  Gly  Arg  Arg
                405                      410                           415

Pro  Ser  Ile  Pro  Leu  Glu  Cys  Ile  Ser  Ile  Pro  Tyr  Pro  Val  Ile  Leu
                420                      425                      430

Pro  Asp  Leu  Glu  Ile  Pro  Gly  Ser  Gln  Ser  Ile  Val  Glu  Asn  Met  Arg
                435                      440                      445

Ala  Val  Ile  Asn  Leu  Ala  Lys  Leu  Thr  Asn  Glu  Ile  Cys  Asp  Ser  Leu
450                      455                      460

Tyr  Trp  Asn  Pro  Ser  Pro  Ser  Phe  Glu  Ser  Gln  Val  Asn  Ser  Val  Arg
465                      470                      475                           480

Arg  Ile  Tyr  Ala  Arg  Leu  Glu  Leu  Trp  Lys  Ser  Asp  Leu  His  Ser  Ser
                485                      490                           495

Val  Val  Phe  Asp  Glu  Ser  Ala  Val  Gln  His  Pro  Leu  Phe  Arg  Ser  Asn
                500                      505                      510

Ala  His  Val  Gln  Met  Ile  Tyr  Asp  Asn  Ala  Ile  Met  Leu  Thr  Thr  Arg
           515                      520                      525

Val  Ile  Met  Val  Lys  Lys  Leu  Lys  Asp  Lys  Asp  Leu  Thr  Ala  Glu  Asn
     530                      535                      540

Arg  Arg  Tyr  Ile  Gln  Leu  Cys  Val  Glu  Ser  Ala  Thr  Arg  Val  Ile  Asn
545                      550                      555                           560
```

```
Ile Ala His Leu Leu Leu Thr His Lys Cys Leu Ser Ser Leu Ser Phe
            565             570                 575
Phe Gly Leu His Val Pro Phe Ala Ser Ala Pro Ile Leu Leu Leu Ser
            580             585                 590
Leu His Tyr Glu Asn Ser Gln Asp Ile Gln Ala Val Val Thr Lys Leu
            595             600                 605
Trp Gln Val Leu Glu Phe Leu Ser Ser Arg Cys Glu Phe Ala Arg Glu
    610                 615             620
Ser Leu Asn Tyr Leu Lys Ser Phe Asn Lys Gln Leu Ser Arg Arg Asn
625             630             635                         640
Ala Pro Asp Ile Asn Asn Pro Ile Ala Asp Phe Gln Asn Ser Phe Gln
                645                 650                 655
Asn Trp Gln Ser Trp Val Gly Asp Met Ser His Gly Asp Met Leu Ser
            660             665             670
Thr Phe Lys Leu Thr Gly Glu Ser Ser Asn Gly Ser Asn Ser Thr Pro
        675             680             685
Asn Glu Ala Phe Gln Pro Phe Asp Gln Thr Ser Ser Leu Tyr Asn Val
    690             695                 700
Pro Gly Leu Asn Lys Ser Tyr Val Ser Asn Gln Pro Ser Leu Leu Thr
705             710             715                         720
Pro Glu Thr Phe Leu Pro Asp Pro Val Leu Asn Leu Glu Val Asp Lys
                725             730                 735
Gln Trp Thr Ala Pro Thr Phe Leu Ser Trp Thr Glu Leu Leu Gly Pro
            740             745                 750
Thr Asn Val Ser Glu Gln Ser Ser His Thr Ala Glu Gln Thr Ser Asn
        755             760                 765
Leu Thr Leu Glu Lys Asn Gly
770             775
```

( 2 ) INFORMATION FOR SEQ ID NO:2:

( i ) SEQUENCE CHARACTERISTICS:
    ( A ) LENGTH: 642 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Schizosaccharomyces pombe pho4 gene ( x i ) SEQUENCE DESCRIPTION: SEQ ID NO:2:

```
CTAATAAATT AAATTGTTGG ATCTTACTAA AGACTAAATA TTAATAATAA TTTTCTCCCA      60
AGCTATTTAT ATACATATTA GAAGCAATTT GCAAAGATAG CAGACTAATA CTCTTCAATG     120
CCCAACTTCT TATTAGTGAT ATACATGTAA AAATATCTTT ATTATGCAAT ATTATGTAGC     180
AGCTCGTACA ATGTTTGCAC ATCTTTACAC AATAGTATTC ATTTTGTATT ACATTATCAT     240
TTATAATTCC ATTTCACAGA GAGTAGGCAT TGCTATTATA TAATATAAAT TTATATAAAA     300
CAAAAAGACT GCAAAATCAT TTCCAACTGA AACTTCGTTC TTTAGTTCTA TTAAATTATT     360
AAGTATTGGA ATATCAGATT TTTGTAAGTT CAGTAATAAT AATATCATTA TATTACACCG     420
TTGTATTATT AATCGCATAA TATTACTGTA ACACTTTGTC CGTAATTTGC ATCGTTATTT     480
CAGTTAACAA TTGTGGGTCC AAAATCTTAA AGTCTAATAG CGAACTACAC CAGGTTTGCA     540
```

ACTTCATTCA TTTTTTTTAA TTCCAATGTA GTCGTGCCGA AATCAGACTT TGGTTTGGTG    600

GTAGCCGGGG TGCTTAGTGT TAGCAGATAT CCGGATTGAT TG    642

( 2 ) INFORMATION FOR SEQ ID NO:3:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: synthetic oligonucleotide OTG2781

( x i ) SEQUENCE DESCRIPTION: SEQ ID NO:3:

AATTCCATTG TCTTGACTAT CACAAACTTT TAAGTCTTTT CTTTTTGGA TCCACACCAT    60

GGAGCTCCCG GGAGATCTA    79

( 2 ) INFORMATION FOR SEQ ID NO:4:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
        ( A ) ORGANISM: synthetic oligonucleotide OTG2782

( x i ) SEQUENCE DESCRIPTION: SEQ ID NO:4:

AGCTTAGATC TCCCGGGAGC TCCATGGTGT GGATCCAAAA AAGAAAAGAC TTAAAAGTTT    60

GTGATAGTCA AGACAATGG    79

( 2 ) INFORMATION FOR SEQ ID NO:5:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: synthetic oligonucleotide OTG2782

( x i ) SEQUENCE DESCRIPTION: SEQ ID NO:5:

GATCCAACCA CATAATGTTC TTGCAAAATT TATTCCTTGG CTTTTGGCC GTCGTTTGTG    60

CCAACGCGTG AGCT    74

( 2 ) INFORMATION FOR SEQ ID NO:6:

( i ) SEQUENCE CHARACTERISTICS:

( A ) LENGTH: 66 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
( A ) ORGANISM: synthetic oligonucleotide OTG2873

( x i ) SEQUENCE DESCRIPTION: SEQ ID NO:6:

CACGCGTTGG CACAAACGAC GGCCAAAAAG CCAAGGAATA AATTTTGCAA GAACATTATG        60

TGGTTG        66

( 2 ) INFORMATION FOR SEQ ID NO:7:

( i ) SEQUENCE CHARACTERISTICS:
( A ) LENGTH: 11 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: synthetic oligonucleotide OTG2874

( x i ) SEQUENCE DESCRIPTION: SEQ ID NO:7:

CGCGATTACG T        11

( 2 ) INFORMATION FOR SEQ ID NO:8:

( i ) SEQUENCE CHARACTERISTICS:
( A ) LENGTH: 9 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
( A ) ORGANISM: synthetic oligonucleotide OTG2875

( x i ) SEQUENCE DESCRIPTION: SEQ ID NO:8:

ATACGTAAT        9

( 2 ) INFORMATION FOR SEQ ID NO:9:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:

( A ) ORGANISM: synthetic oligonucleotide OTG3569

( x i ) SEQUENCE DESCRIPTION: SEQ ID NO:9:

TTTGGGCATG CGTCTTTTGA TGCTAAATAA ATTAAATTGT TGG    43

( 2 ) INFORMATION FOR SEQ ID NO:10:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
        ( A ) ORGANISM: synthetic oligonucleotide OTG3239

( x i ) SEQUENCE DESCRIPTION: SEQ ID NO:10:

GAGAAATACC ACTTAACTTC ATGGATCCCG AGAAAAACA ATG    43

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
        ( A ) ORGANISM: synthetic oligonucleotide OTG3210

( x i ) SEQUENCE DESCRIPTION: SEQ ID NO:11:

CCCAAACCAT GGCAATCAAT CCGGATATCT GCTAAC    36

( 2 ) INFORMATION FOR SEQ ID NO:12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: synthetic oligonucleotide OTG4645

( x i ) SEQUENCE DESCRIPTION: SEQ ID NO:12:

AAACAAGCAT GCGTTTGGTG GTAGCCGGGG    30

( 2 ) INFORMATION FOR SEQ ID NO:13:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: synthetic oligonucleotide OTG4646

(x i) SEQUENCE DESCRIPTION: SEQ ID NO:13:

AAACAAGCAT GCTCATTCAT TTTTTTTAAT TCCAATGTAG     40

(2) INFORMATION FOR SEQ ID NO:14:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: synthetic oligonucleotide OTG4647

(x i) SEQUENCE DESCRIPTION: SEQ ID NO:14:

AAACAAGCAT GCGGTCCAAA TCTTAAAGTC TAATAGCG     38

(2) INFORMATION FOR SEQ ID NO:15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: synthetic oligonucleotide OTG4648

(x i) SEQUENCE DESCRIPTION: SEQ ID NO:15:

AAACAAGCAT GCTACTGTAA CACTTTGTCC GTAATTTGC     39

(2) INFORMATION FOR SEQ ID NO:16:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: synthetic oligonucleotide OTG4649

(x i) SEQUENCE DESCRIPTION: SEQ ID NO:16:

AAACAAGCAT GCCACAGAGA GTAGGCATTG CTATT     35

( 2 ) INFORMATION FOR SEQ ID NO:17:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: synthetic oligonucleotide OTG4924

( x i ) SEQUENCE DESCRIPTION: SEQ ID NO:17:

```
CAGCCGGGGT GCTTAGTGTT AGCAGATATC CGGATTGATT GC                 42
```

( 2 ) INFORMATION FOR SEQ ID NO:18:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
        ( A ) ORGANISM: synthetic oligonucleotide OTG4925

( x i ) SEQUENCE DESCRIPTION: SEQ ID NO:18:

```
CATGGCAATC AATCCGGATA TCTGCTAACA CTAAGCACCC CGGCTGCATG         50
```

( 2 ) INFORMATION FOR SEQ ID NO:19:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: synthetic oligonucleotide OTG5296

( x i ) SEQUENCE DESCRIPTION: SEQ ID NO:19:

```
CGGCCCATGG TTTGGTGGTA GCCGGGGTGC TTAGTGTTAG CAGATATCCG GATTGATTGC   60

CATGGCCTC TC                                                        72
```

( 2 ) INFORMATION FOR SEQ ID NO:20:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO

-continued ( i v ) ANTI-SENSE: YES ( v i ) ORIGINAL SOURCE:
    ( A ) ORGANISM: synthetic oligonucleotide OTG5297

( x i ) SEQUENCE DESCRIPTION: SEQ ID NO:20:

| | | | | | |
|---|---|---|---|---|---|
| AGGCCCATGG | CAATCAATCC | GGATATCTGC | TAACACTAAG | CACCCCGGCT | ACCACCAAAC | 60 |
| CATGGGCCGG | AG | | | | | 72 |

( 2 ) INFORMATION FOR SEQ ID NO:21:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: synthetic oligonucleotide OTG5217

( x i ) SEQUENCE DESCRIPTION: SEQ ID NO:21:

CCCAAAGCAT GCAAGCTTAA AGGAATCCGA TTGTCATTC        39

( 2 ) INFORMATION FOR SEQ ID NO:22:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
        ( A ) ORGANISM: synthetic oligonucleotide OTG3028

( x i ) SEQUENCE DESCRIPTION: SEQ ID NO:22:

ATCTTGTTAG TAGCCATGGA TCCGATTTAA CAAAGCG        37